Aug. 1, 1972 S. F. HENSON Plant Pat. 3,247
AZALEA PLANT
Filed Nov. 23, 1970
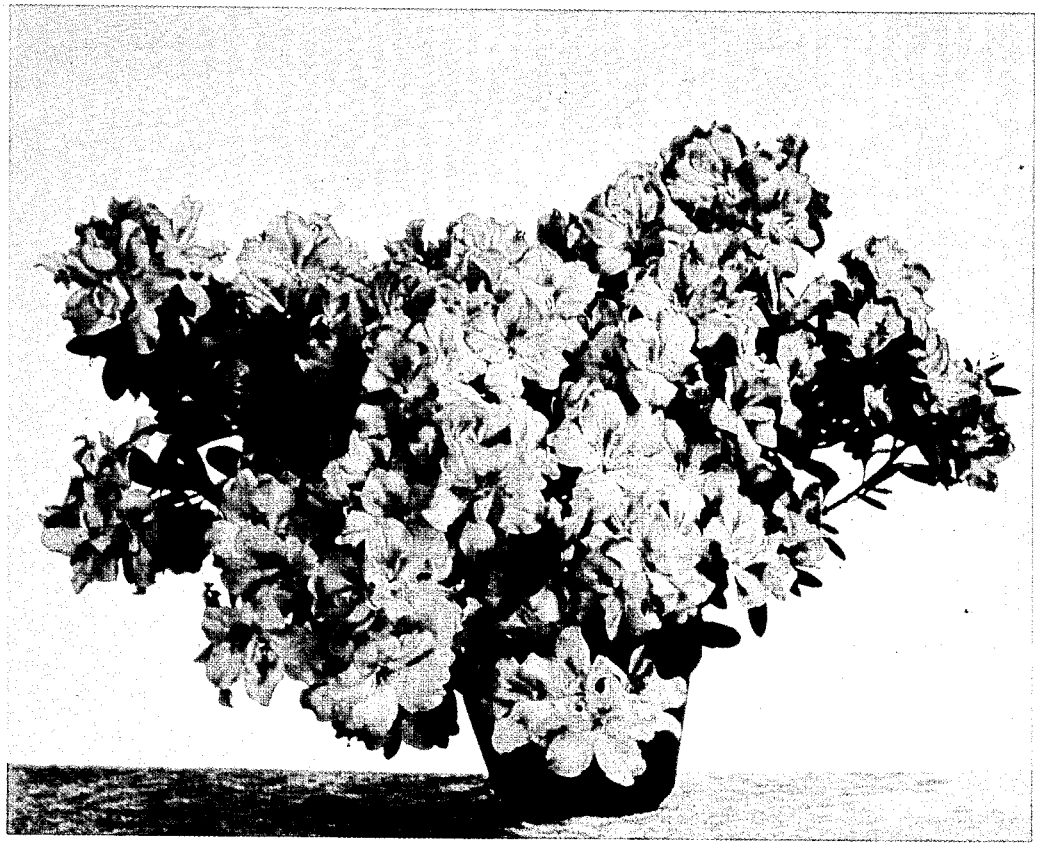
INVENTOR
STUART F. HENSON
BY
Oberlin, Maky, Donnelly & Renner
ATTORNEYS

United States Patent Office

Plant Pat. 3,247

Patented Aug. 1, 1972

3,247

AZALEA PLANT

Stuart F. Henson, Fallbrook, Calif., assignor to Yoder Brothers, Inc., Barberton, Ohio

Filed Nov. 23, 1970, Ser. No. 92,331

Int. Cl. A01h *5/00*

U.S. Cl. Plt.—56 1 Claim

The present invention comprises a new and distinct variety of azalea plant which has resulted from crossing certain azalea selections in a program of controlled hybridization. The seed parent is an unnamed seedling from the progeny of the cross Mme Van Der Cruyssen, an unpatented Belgian Indica, crossed with Rose Queen, an unpatented Rutherfordnana, and the pollen parent is an unnamed seedling from the progeny of the cross of an unnamed seedling crossed with Rose Queen.

The new variety is similar in many respects to Skylark, an unpatented but well-known commercial variety, having the same characteristics as Skylark of rapid growth, informal growth habit and excellent keeping qualities.

The new variety is distinguished from Skylark by the following characteristics:

1. Needs no growth regulators for budding and growth control. Growth regulators are generally advisable for Skylark to control growth.
2. Is two-tone pastel light pink and white with a contrasting deep blotch compared to the medium pink color of Skylark.
3. Buds up easier and responds several weeks earlier in natural season and year round flowering programs.
4. A more horizontal though not cascading growth habit.

The new variety is distinguished from Constance, an unpatented variety, by the following characteristics:

1. Longer keeping qualities than Constance
2. Earlier response
3. More delicate light pink color The new variety was selected from a progeny of seedlings from the above mentioned parents. Varietal worth was determined by flowering liners built up from the initial selection in both year round and natural season flowering programs over a period of 5 years. Stock growth was evaluated in the vicinity of Fort Myers, Florida.

My new variety has been asexually reproduced by cuttings at Fallbrook, California, and has been found to retain its dinstinctive characteristics through successive propagations.

My new variety when grown in the vicinity of Barberton, Ohio, has a response described as early-mid season, although it will be understood that the response time and blooming period may vary significantly with varying environmental conditions such as temperature day length and light intensity. Suggested flowering period is mid-December through April in a natural season program and year round (12 months) in a controlled flowering program.

The accompanying drawing shows the unique characteristics of my new variety, the colors being as nearly true as possible with color illustrations of this type.

The following is a detailed description of my new variety based on observations made of the new variety in a greenhouse in northeastern Ohio. The color references are to the Munsell Color Book, 1963 edition, and the Ridgway Color Standard and Nomenclature, 1912 edition.

Botanical classification: *Rhododendron hybrida*, evergreen type.

| Flower | Munsell | Ridgway |
|---|---|---|
| Color: (Spring color at Barberton, Ohio) | A warm pink | Deep rose pink. |
| General tonality | A warm pink, nearest to 5RP6/12 | Deep rose pink 71d. |
| Sepals first divide | Pink—7.5RP6/10 | |
| Petals unfurl | Pink, nearest to 8.25R5/14 but lighter | Rose-spinel rose 71b–71'b. |
| Inside petals (fully open) | Pink, near 5RP6/12 but not as gray | Rose 71b. |
| Reverse petals (fully open) | Light rose-pink near 5RP6/12 not gray, but lighter | Lighter than 71b. |
| Base of petals | Blush 5RP9/1 (almost white) | |
| Blotch | Deep rose 10RP4/14 but darker | |
| Discoloration | Retains color for 3 weeks with gradual fading. As flowers age in a bright greenhouse, color fades to a light pink. | |

Bud:

*Size*—Medium.
*Form.*—Pointed.
*Opening habit.*—Opens cup-like, retains cup-like form.

Bloom:

*Size.*—Medium.
*Average.*—2¼"; range, 1¾"–2¾".
*Borne.*—Several together; average, 3; range, 1–4.
*Form.*—Semi-double with varying degrees of petaloid anthers.

Blooming habit: Once, profusely. Response—natural season, early to mid season. Christmas flowering possible in all areas. Year round—early, all 12 months; buds easily and uniformly over wide range of conditions.

*Sepals.*—Normal, smooth edge. Aspect, hairy; dry up and fall off as buds open.
*Peduncle.*—Length, long; aspect, hairy; strength, strong.

Petals:

*Texture.*—Soft.
*Appearance.*—Inside, satiny; outside, satiny.
*Form.*—Rounded with wavy margins (somewhat ruffled in appearance).
*Arrangement.*—Imbricate with petaloids.
*Fragrance.*—None.
*Persistence.*—Hange on and dry. Non-shattering.
*Longevity.*—Greenhouse, 3 weeks; home 4–5 weeks.

*Reproductive organs*

Stamen anthers: 5–10. Variable; generally petaloid, light tan 5YR8/4.
Filaments: Thin, somewhat pubescent, very light green, 2.5GY2/9.
Style: Columnar. May be greatly reduced in size and fasciated. Very light green 2.5GY2/9.
Stigmas: Normal, may be fasciated. Yellow green, near 5GY8/6.
Ovaries: Hypogynous.

*Plant*

Bush form:

*Growth habit.*—Informal and horizontal rather than upright, but not cascading.
*Breaking habit.*—Vigorous, informal.

*Size.*—Average finished product grown from the standard #7 liner of Yoder Brothers, Inc., Barberton, Ohio. Height—10"–12"; diameter—12"–16".
*Budding ease.*—Quite easy under a wide range of conditions.

Rooting habit: Good, easy, growth from own roots, vigorous excellent uniformity of budding growth regulator not needed for budding.

Foliage:

*Type.*—Evergreen.
*Leaflets.*—Single.
*Size.*—Length, average 2"; range 1½"–2½" width, average ¾", range ½"–1".
*Shape.*—Obovate to oblanceolate.
*Texture.*—Upper—glossy; lower—smooth.
*Rib and veins.*—Slightly depressed.
*Edge.*—Smooth.
*Color.*—New foliage, upper—green, near 5GY4/6; lower—green, 5GY5/4; mature foliage, upper—dark green, 7.5GY2/4; lower—green, near 5GY5/4.
*Petiole.*—Rather long, green, 5GY5/6.

Stems:

*Color of new wood.*—Green, 5GY7/6.
*Color of mature wood.*—Brown, near 10YR5/6.

Recommended flowering period:

*Year round.*—All 12 months in controlled programs.
*Natural season.*—December through April. Can be flowered for Christmas in all areas of the United States.

*Responsiveness to day length and temperature.*—Buds under wide range of conditions.

Cooler tolerance: Excellent.
Shipping tolerance: Excellent.

I claim:

1. A new and distinct variety of azalea characterized particularly as to novelty by its rapid growth, it warm pink color, the long-lastingness of its flowers, its non-shattering trait, its evergreen type foliage, its early mid-season profuse flowering, and its adaptibility to year round flowering programs.

No references cited.

ROBERT E. BAGWELL, Primary Examiner